(12) United States Patent
Ebersole et al.

(10) Patent No.: US 8,211,366 B2
(45) Date of Patent: Jul. 3, 2012

(54) APPARATUS AND METHODS FOR TESTING IMPURITY CONTENT IN A PRECIOUS METAL

(75) Inventors: Michael R. Ebersole, Annville, PA (US); Warren D. Kleinfelter, Palmyra, PA (US)

(73) Assignee: Kee Gold Corp., Cleona, PA (US)

( * ) Notice: Subject to any disclaimer, the term of this patent is extended or adjusted under 35 U.S.C. 154(b) by 459 days.

(21) Appl. No.: 12/546,307

(22) Filed: Aug. 24, 2009

(65) Prior Publication Data

US 2011/0042240 A1 Feb. 24, 2011

(51) Int. Cl.
*G01N 27/403* (2006.01)

(52) U.S. Cl. ........................ 422/82.02; 324/693; 204/400

(58) Field of Classification Search .................. 324/446, 324/450, 437, 691, 693, 696, 724; 422/82.02–82.03; 204/400, 416–419
See application file for complete search history.

(56) References Cited

U.S. PATENT DOCUMENTS

| | | | |
|---|---|---|---|
| 3,575,834 A | 4/1971 | Hoole et al. | |
| 4,162,211 A | 7/1979 | Jerrold-Jones | |
| 4,376,027 A | 3/1983 | Smith et al. | |
| 4,627,892 A | 12/1986 | Worrell et al. | |
| 4,786,374 A | 11/1988 | Worrell et al. | |
| 4,799,999 A | 1/1989 | Medvinsky et al. | |
| 5,080,766 A | 1/1992 | Moment et al. | |
| 5,218,303 A | 6/1993 | Medvinsky | |
| 5,716,513 A | 2/1998 | Reiss | |
| 5,888,362 A * | 3/1999 | Fegan, Jr. | 204/400 |
| 6,051,126 A | 4/2000 | Fegan, Jr. | |
| 6,103,194 A | 8/2000 | Jackson | |
| 6,143,572 A | 11/2000 | Grand et al. | |
| 6,930,486 B2 * | 8/2005 | Muscarella et al. | 324/446 |
| 2007/0261958 A1 | 11/2007 | Jiang et al. | |

FOREIGN PATENT DOCUMENTS

GB 2218210 A * 11/1989

* cited by examiner

*Primary Examiner* — Alex Noguerola
(74) *Attorney, Agent, or Firm* — Haynes and Boone, LLP (57) ABSTRACT

A precious metal testing apparatus and methods adapted to analyze impurities in a precious metal test sample is described. The testing apparatus contains a test probe that has a replaceable portion and that is connected to a meter to measure resistance. The replaceable portion contains or forms a reservoir that includes at least one electrolyte component, a conductive member, and a fibrous tip. The electrolyte component is fluidly associated with a fiber tip and the conductive member contacts an electrical contact located outside the reservoir. Methods of testing and instructions regarding such methods are also included.

20 Claims, 3 Drawing Sheets

APPARATUS AND METHODS FOR TESTING IMPURITY CONTENT IN A PRECIOUS METAL

TECHNICAL FIELD

Apparatuses and methods adapted to test the impurity content of a precious metal component. More particularly, the apparatus and methods include replaceable cartridges and the replacement of cartridges.

BACKGROUND OF THE INVENTION

Due to their chemical and physical properties, precious metals are increasingly used in a variety of industries, including jewelry, art, coinage and exchange, fuel cells, man-made fibers, computers and other electronics, medicine and pharmaceutical products, and manufacturing. The unique properties of precious metals, along with their relative scarcity, dictate a high demand and value in the marketplace. Alloying a precious metal with one or more other metals or non-metals, or plating or washing an article with a precious metal to increase aesthetic appearance is often done to reduce expense but can result in non-uniform distribution of precious metals throughout an article and articles of dubious provenance are often poorly prepared. This can often alter properties of such objects, and can be particularly detrimental to the functioning of articles that will be used for functional purposes beyond mere aesthetic appearance, such as noted above. It can also affect even the value of aesthetic articles, such as jewelry, art, and coinage depending on the impurity content present. Determining the composition of precious metallic samples and items accurately and quickly, while minimizing the alteration of the sample in the process, is desirable when evaluating the sample for potential usefulness and pricing.

There are some long-standing analytical techniques currently available to determine the nature, content and components of items that contain precious metals. Some analytical methods use an electrochemical process to evaluate the purity of precious metals. For example, U.S. Pat. No. 4,799,999 teaches a method whereby the specimen is wetted with an electrolyte, a small current then anodizes the surface of the specimen for a metered period of time, a sensing device is then applied to the charged surface and observes the potential decay, which is then interpolated with empirical data to determine the karat quality of a gold alloy.

As another example, U.S. Pat. No. 5,218,303 concerns a method where a controlled amount of electrolyte is deposited on a sample of precious metal alloy, an electrode is placed in contact with the sample and electrolyte through which an electric current is applied to create an electrolyte paste. As the current decays to an asymptotic level, a second and third pulse of electric current are applied and the measured electrical conductance is compared to a table of standards.

Another testing device includes a handheld applicator to apply a testing solution. For example, U.S. Pat. No. 6,103,194 concerns a handheld applicator for testing metallic items and includes a housing that surrounds an insert containing a reservoir with a testing chemical and an applicator, which applies the testing chemical to the surface of the metal.

U.S. Pat. No. 5,888,362 concerns a handheld probe having an electrode embedded in an electrolyte in a reservoir of the probe and arranged to conduct electrically with the sample through the electrolyte and a fibrous tip. A battery is coupled to a calibration potentiometer and the sample in circuit to form a galvanic cell.

These devices have one or more limitations that have prevented them from gaining widespread acceptance in the industry. Thus, an improved testing device and methods according to the invention described below have been desired to expedite economical testing of precious metal objects.

SUMMARY OF THE INVENTION

The invention encompasses a precious-metal testing apparatus adapted to analyze an impurity content of a precious metal sample, which includes a test probe having a probe end and a connection end, wherein the test probe includes a housing and a cartridge including a conductive member, a supply of an electrolyte component, and a casing retaining the electrolyte component, a portion of the conductive member, and an end of a fibrous tip at the probe end in fluid communication with the electrolyte component, wherein the cartridge is retained by the housing, and wherein the fibrous tip is electrically conductive when a sufficient amount of the electrolyte component is present therein, along with preferably a meter adapted to measure an electrical resistance of a precious-metal sample through the test probe, an electrical connection that electrically associates the conductive member of the cartridge, which extends through an end thereof opposite the probe end, with an external conductive component that extends to the meter, wherein the electrical connection is located outside the casing that contains the electrolyte component.

In one embodiment, a portion of the test probe is replaceable so as to permit replenishment of the supply of the electrolyte component. In another embodiment, the conductive member includes palladium, silver, or a mixture thereof. In another embodiment, the test probe is releasably connected to the external conductive component. In a preferred embodiment, the housing includes a closed position to retain the cartridge and an open position configured to release the cartridge for replacement thereof. In yet another preferred embodiment, the housing includes a plurality of pieces that can threadedly couple to form the closed position and uncouple to attain the open position.

In another embodiment, the fibrous tip is at least substantially free, or entirely free, of an epoxy. In another embodiment, the fibrous tip is at least substantially free, or entirely free, of any resin that hardens the tip over time or through exposure to the atmosphere or the electrolyte component. In one preferred embodiment, the test probe and electrically conductive portions thereof are at least substantially, preferably entirely, corrosion resistant. In yet another embodiment, the apparatus further includes an integrated file associated with the test probe for minimizing or removing a contaminant portion from the test sample.

The invention also encompasses a method for analyzing an impurity content of a precious metal sample, which method includes associating an electrically conductive zone of a portable testing device with the sample, wherein the electrically conductive zone is detachable from the remainder of the testing device is replaceable, measuring the electrical resistance of the test sample, and comparing the measured resistance to a standard value of electrical measurements including at least one of the same type of precious metal to determine the impurity content of the sample. In one embodiment, the method further includes displaying the measured resistance to a user. In another embodiment, the method further includes removing at least a portion of a contaminant component from a surface of the sample before measuring.

The invention further encompasses a replaceable, impurity content testing cartridge sized and configured to fit a precious metal test probe that includes a non-conductive casing including an electrolyte component present in an amount sufficient to conduct electricity through a portion thereof, a conductive member electrically associated with the electrolyte component and oriented at least partly along a length of the casing so that a portion of the conductive member extends through the casing so as to minimize loss of the electrolyte component, and an electrically non-conductive fiber tip at least partially contacting the electrolyte component through an aperture in the opposite end of the casing, wherein the fiber tip is electrically conductive when a sufficient amount of electrolyte component is absorbed therein, and wherein the portion of the conductive member that extends through the casing is adapted for electrical connection in an environment that is at least substantially free, preferably entirely free, of electrolyte component.

In one embodiment, the replaceable cartridge further includes a fibrous material that at least partially surrounds the conductive member in the casing to inhibit the loss of electrolyte component from the casing. In another embodiment, the electrically non-conductive fiber tip includes a plurality of at least substantially parallel elongated fiber portions pressed together. In a preferred embodiment, the plurality of fiber strings include an acrylic component. In another embodiment, different acrylic components can be used in different fiber strings.

In yet another embodiment, the conductive member includes palladium, platinum, or silver, or a combination thereof. In a preferred embodiment, the conductive member includes a first metal in a core layer and a second, different non-corrosive metal that surrounds the first metal to inhibit or prevent contact between the core layer and the electrolyte component in the casing. In another preferred embodiment, the cartridge further includes an electrical contact that includes the same material as the conductive member and is electrically associated therewith.

In a further embodiment, the electrolyte component includes an aqueous acidic solution. In a preferred embodiment, the aqueous acidic solution includes at least one of ammonium chloride (NH4Cl), hydrochloric acid (HCl), nitric acid (HNO3), or any combination thereof. In a more preferred embodiment, the aqueous acidic solution includes ammonium chloride (NH4Cl) and distilled water, preferably as a solution of saturated ammonium chloride.

The invention also encompasses a method for repairing the precious-metal testing device of claim 5 which includes adjusting the housing of the test probe into the open position, removing the replaceable cartridge from the test probe, inserting a replacement cartridge within the housing, and returning the housing to the closed position so as to retain the replacement cartridge.

The invention further encompasses a set of instructions to carry out any of the methods discussed herein, along with the precious-metal testing device, the test probe, or the replaceable cartridge, as applicable, operably associated with the instructions.

BRIEF DESCRIPTION OF THE DRAWINGS

The present disclosure can be better understood from the following detailed description when read with the accompanying figures. It is emphasized that various features are not drawn to scale and are used only for illustrative purposes. In fact, the dimensions of the various features may be arbitrarily increased or reduced for clarity of discussion.

DETAILED DESCRIPTION OF PREFERRED EMBODIMENTS

The apparatus and methods described herein facilitate more accurate testing of an impurity content in and on precious metal object(s) via a stable test probe that contains a supply of an electrolyte component that includes at least one electrolyte, and that resists corrosion over an extended period of time. A portion of the test probe is replaceable to replenish the supply of electrolyte(s), and this can be a replaceable cartridge disposed at least partially within the test probe or it can be the entire test probe. The test probe contains a probe end that contacts a precious metal object to be tested and a connection end that includes or forms an electrical connection to an electrical meter. The cartridge can form a portion of the reservoir along with the tip housing and conductive member. Preferably, however, the cartridge contains a self-contained reservoir that includes the supply of the electrolyte component that is sufficient to conduct electricity from a tip at the probe end to a conductive member disposed in or adjacent to the reservoir, which conductive member conducts electricity to the connection end of the test probe. The test probe can preferably be releasably electrically connected to a conventional meter. A portion of an outer surface of the replaceable cartridge can be electrically associated with the meter so as to minimize corrosion at the electrical connection.

The electrical conduction between two different precious metals or precious metal-containing alloys, or a combination thereof, one part of the test probe and the other being the test sample, can be compared, measured and quantified by a conventional meter as described elsewhere (See, for example U.S. Pat. No. 5,888,362, the contents of which are incorporated herein by express reference thereto regarding operation and construction of suitable meters).

The configuration and replaceability of the test probe or a portion thereof allows for greater variability in the type and size of precious metal(s) to be tested because different size test probes can be used. Additionally, this can advantageously provide increased portability and even facilitate replacement when the supply of electrolyte(s) is in need of replenishment. By arranging the electrical connection of the conductive member to a connection end of the cartridge to electrically connect to the meter outside the reservoir, this can and preferably does minimize or avoid corrosion that typically occurs in electrolyte-containing test devices. An exemplary embodiment of the invention is discussed below.

Figure 1:
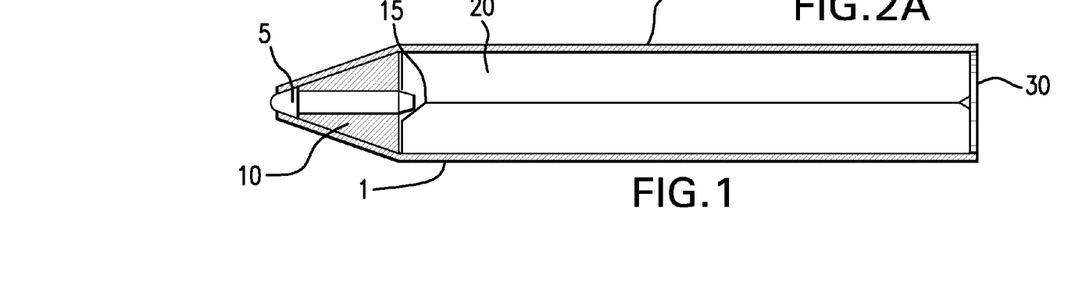
FIG. 1 illustrates a sectional view of a replaceable cartridge according to the invention.

FIG. 1. illustrates a sectional view of an embodiment of a replaceable cartridge 1 that is placed inside a housing of the test probe. The replaceable cartridge 1 includes at least a reservoir 20 that contains at least one electrolyte and preferably, a fibrous material associated therewith, a conductive member 15 that is operably and electrically associated with a tip 5 at the probe end and is connected to a contact 30 at the connection end, along with a tip housing 10 adapted to position the tip 5 properly and an outer casing 25 that at least substantially contains the reservoir 20 and is attached to the tip housing 10.

The electrolyte component is typically a solution in the reservoir 20. The electrolyte component can include any suitable electrically conductive liquid material that can be dispensed through the tip, but is typically acidic. The electrolyte component is preferably at least one of ammonium chloride ($NH_4Cl$), hydrochloric acid (HCl), nitric acid ($HNO_3$), or any combination thereof. An exemplary electrolyte component is a solution formed by adding ammonium chloride ($NH_4Cl$) into distilled water until the solution is saturated. Typically, under ambient conditions (e.g., 68° F. and atmospheric pressure), this will be about 40.8% by weight ammonium chloride and about 59.2% by weight distilled water. Different concentrations will be preferred for use in different temperatures, elevations, and if a different electrolyte component is included, each of which can be determined by one of ordinary skill in the art, particularly in view of the guidance provided herein. The casing (or housing) is preferably at least substantially, or entirely, free of a gel.

A plurality of the fibers in the reservoir 20 are preferably oriented in substantially the same direction, or the same, direction. A preferred direction for the plurality of fibers is at least substantially parallel, or parallel, to one another. In this regard, "substantially" refers to an angle between two fibers of less than about 30 degrees, preferably less than about 15 degrees, and more preferably less than about 5 degrees. Preferably, the fibers are oriented longitudinally in the direction of the fiber tip 5 and the contact 30 at the other end of the cartridge 1. Preferably, the directional fibers in the tip 5 are prepared by pressing a plurality of smaller fibers together to form a tip of desired thickness or diameter. The fibers can be made of any of a variety of natural or synthetic fibers or combinations thereof available to those of ordinary skill in the art. The fibrous tip 5 is at least substantially free, and preferably entirely free, of epoxy or resin. Preferably, the tip 5 is at least substantially free, preferably entirely free, of any resin that increases the hardness of the tip over time, or upon repeated exposure to the atmosphere or the electrolyte component.

Preferably the fibers used to form the tip and the fiber material in the reservoir 20 include silk or corn silk. The tip and fiber material in the reservoir 20 are independently selected and can be the same or different. In one embodiment, it is preferred that these are the same. The tip and fiber material in the reservoir can be integrally formed to facilitate wicking the electrolyte component from the reservoir 20 through the tip 5 to the test sample.

The reservoir 20 is in contact with at least a portion of the electrically non-conductive absorbent fiber tip 5. Suitable fiber tips 5 can preferably include acrylic fiber material, such as that commercially available from Teibow of Japan (e.g., Product No. TCE470C) or Porex Technologies of Fairburn, Ga. A portion of the end of the fiber tip 5 opposite the probe end extends into the reservoir 20. The portion can be the whole or only a part of the tip. The tip housing 10 functions as a "spacer" to help properly position the fiber tip 5 within the tip housing 10 so that the end is in alignment and in fluid communication with the reservoir 20. The electrolyte component present in the reservoir 20 can be absorbed at the end of the fiber tip 5 by capillary action. Once an amount of the electrolyte component is absorbed by the fiber tip 5, the probe end (i.e., the exposed end that contacts the test sample) of the fiber tip 5 can be positioned adjacent or preferably contacting the test sample to complete an electrical circuit so that a reading on the meter can be obtained. The fiber tip 5 is partially encased in the tip housing 10 so as to help manage only a sufficient flow of the electrolyte into the fiber tip 5, as excessive flow will render the test probe inoperative sooner as the electrolyte component is depleted faster. The tip housing 10 can be made of any non-conductive material, in one embodiment preferably a plastic material and more preferably a polymer such as polypropylene, polyethylene, or a combination thereof. A suitable polypropylene is commercially available from Lyondellbasell (e.g. Product Pro-fax™ PD626), which can be shaped as desired through conventional molding, injection, or another formation technique available to those of ordinary skill in the art.

Figure 8A:
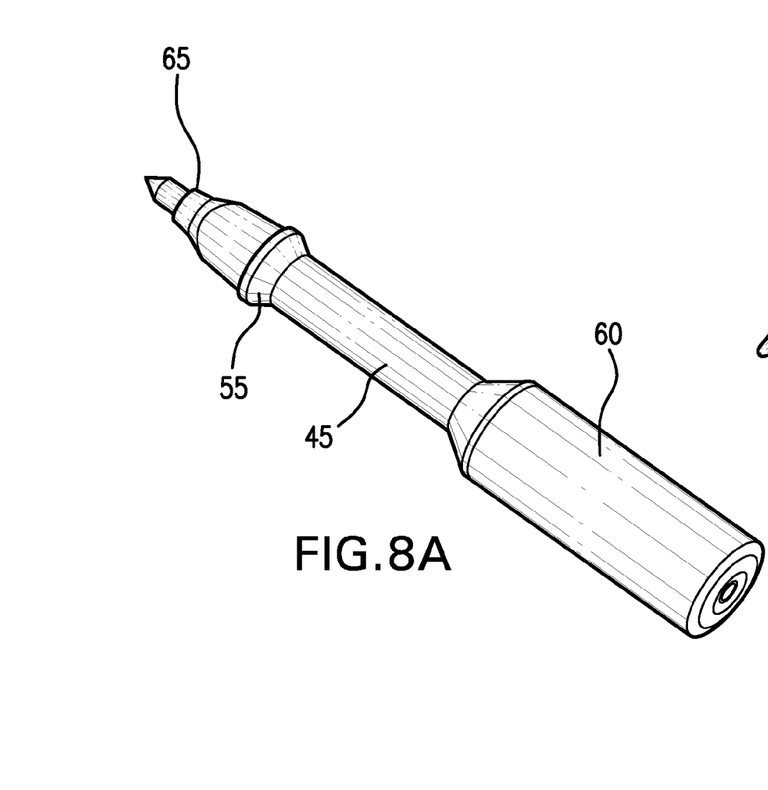
FIGS. 8A and 8B illustrate three dimensional views of the assembled test probe, according to varying embodiments of the invention.
Figure 8B:
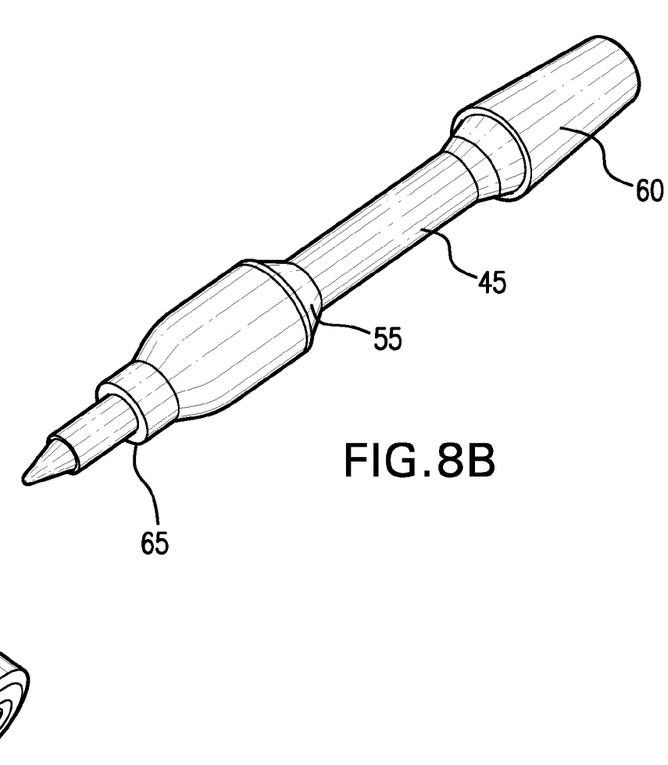

The reservoir 20 is at least partially sealed, and preferably entirely sealed to minimize or avoid loss of electrolyte component except through the tip during operation of the test apparatus. In fact, an operatively associated covering 65 (as shown in FIGS. 8A and 8B) can be used with the test probe and used to cover the tip when not in use to further restrict loss of electrolyte component. Preferably, the reservoir can be defined by a casing 25 that extends around a zone containing the electrolyte component. Preferably, the reservoir 20 can be contained primarily by the outer casing 25 in a zone that is any three-dimensional shape including one that is substantially or entirely cylindrical, spherical, oblong, oval or capsule-shaped. Preferably, the zone is at least substantially cylindrically shaped, or cylindrically shaped, so as to best fit a user's grasp like a writing implement or dental tool. The substantially cylindrical shape can be, for example, like a pencil having about five to nine facets around the circumference of the cylinder. Whether or not the zone has circular cross-sections of similar diameter, the housing or a portion thereof (discussed below) can be arranged to have the desired shape and have internal projections to match and retain the outer casing 25 to help retain it in a fixed position relative to the other components in the test probe. The reservoir 18 and the casing 25 can be independently selected from any available substantially or entirely non-conductive material, preferably a glass or a plastic component of one or more glass or plastic materials. A plastic component is preferred as it is less likely to shatter, however, it must be a suitable plastic with low moisture migration potential to inhibit drying of the electrolyte component. More preferably, the casing 25 includes polypropylene, polyethylene, or a combination thereof. Suitable material is commercially available from, for example, Filtrona Porous Technologies of Colonial Heights, Va. The casing 25 preferably is sized and shaped to match the reservoir 18. In one embodiment, the casing 25 has at least one aperture, and preferably only one aperture, at the probe end to facilitate flow of the electrolyte component into the fiber tip 5. In another embodiment, multiple tips (not shown) can be used and the casing 25 would have multiple apertures (not shown)

at the probe end sized and dimensioned to permit these multiple tips to extend therethrough. Thus, reference herein to a "tip" could also be understood to refer to multiple such tips, although a single tip is preferred in most embodiments. To a user, however, the multiple tips might be sufficiently small and arranged sufficiently closely together that they would appear to be a single tip except upon closer examination or using magnifying equipment. The electrolyte component can then be repeatedly dispensed as needed when the test probe is used to contact different precious metal test samples. In each case, the tip housing 10 is preferably sized and dimensioned to closely fit the tip 5 so as to minimize excess space around the tip that could facilitate the undesirable escape of electrolyte component or corrosive gases generated by the electrolyte component in the tip. Thus, the tip housing 10 is preferably sized to have a chamber only large enough to fit the tip 5 and so that the tip 5 at least substantially, preferably entirely, fills the chamber in the tip housing 10. The tip housing 10, and associated tip cap 55, however, can have a similar or different shape than that of the adjacent and complementary casing 25 and housing 45 that surround the reservoir 20. As seen in FIGS. 8A and 8B below, the housing 45 can be cylindrical but recessed from the operatively associated tip cap 55 and tip covering 65. The tip 5 will preferably contain a portion that projects beyond an end of the tip housing 10 and in towards and into the reservoir. This projection 12 in FIG. 2A (discussed below), preferably is open on a portion of the projection to permit fluid communication of the electrolyte component with the tip 5.

Through the reservoir 20 extends a conductive member 15 that helps conduct electricity between the meter and the test sample. The conductive member is typically a corrosion-resistant metal component because it must contact the electrolyte component to exchange electrical current with the tip. The conductive member can take any suitable shape, but is preferably primarily an elongated bar, strand, wire, tube, or the like. The conductive member 15 is preferably palladium, platinum, or silver, or a combination thereof, and preferably palladium or silver, or a combination thereof. In a preferred embodiment, the conductive member 15 includes a strand of conducting palladium such as that commercially available from Union City Filament Corporation of Ridgefield, N.J. It is also possible to make the conductive member 15 of one or more layers. It can be formed of any conductive material(s) as a core layer, or even non-conductive material as a core layer that forms a backbone that is completely surrounded by, or plated with, one or more corrosion-resistant materials, preferably one of the above-noted metals, or a combination thereof, to minimize or avoid any conductive core layer contact with the electrolyte component. A conventional, less expensive conductive material such as copper, and more preferably nickel-plated copper, is typically used at the connection end of the test probe to connect with the conventional meter because of cost considerations, but a change from a corrosion-resistant metal component in the conductive member to a more cost efficient conductor is preferably achieved between the conductive member at least partly disposed the cartridge and the meter. This connection is preferably arranged to minimize or avoid contact with the electrolyte(s) and any gas generated therefrom. Thus, the connection preferably occurs between a conductive portion of the casing 25 or the test probe (not shown), and a conventional wire outside but adjacent and in electrical communication with the cartridge. The connection can be a banana clip or plug, such as that available from Pomona Electronics of Everett, Wash. (e.g., Product No. 72930), made of any suitable material known to those of ordinary skill in the art, preferably copper and more preferably nickel plated copper, or any other suitable device available to those of ordinary skill in the art to facilitate connection of the two distinct types of conductive materials in the conductive member and the electrical connection from the test probe to the test meter.

The conductive member 15 preferably contacts the electrical contact 30 so as to transmit electrical signals to and from the meter. The conductive member 15 can be doubled up, looped, braided, or placed in any other suitable arrangement at the end of the cartridge adjacent the electrical contact 30 to help ensure sufficient electrical conductivity. Preferably, the arrangement of the conductive member 15 will help minimize the impact of the corrosive environment in the cartridge 1 on the conductive member 15. This arrangement can provide a compression spring-like action to facilitate maintaining the conductive member 15 in touch with the electrical contact 30. The conductive member 15 may touch the sides of the casing 25 without affecting the readings from the sample. The replaceable cartridge 1 is arranged inside the housing of the test probe, to be described below. It should be understood that the conductive member 15 could exit the casing 25 at any point, such as by extending along a radius of the casing 25 and through a side location of the casing 25, at which point it could extend longitudinally towards the connection on the outside of the casing 25 but inside the housing. In fact, the connection with the conventional wire that leads to the tester could occur at any location along the outside of the casing, but preferably it is positioned as depicted at the end of the casing 25 opposite the probe end where the tip 5 is located.

Figures 2A, 3:
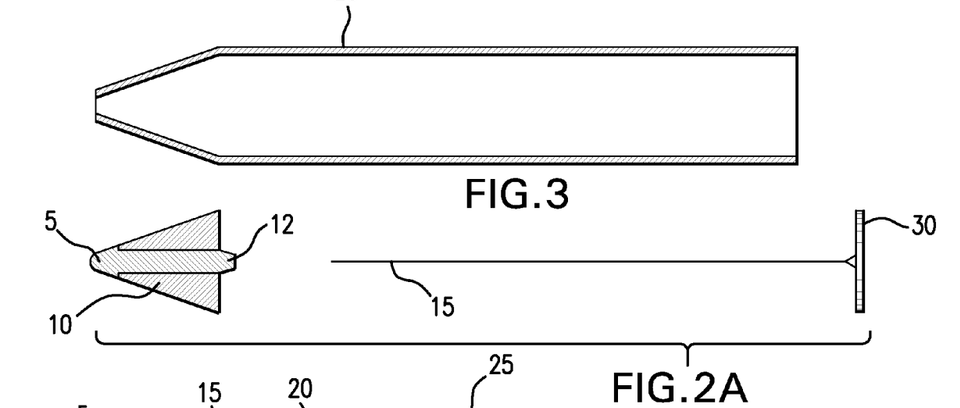
FIG. 2A illustrates a sectional view of a tip housing in relation to a conductive member which is associated with an electrical contact according to the invention.
FIG. 3 illustrates a sectional view of an outer casing that surrounds a reservoir for electrolyte component and at least a portion of the tip according to the invention.

With reference to FIG. 2A, the conductive member 15 can extend the entire length of the reservoir 20 from the contact 30, can terminate in the reservoir 20 in the form of an at least partial loop (see FIG. 4) or a complete loop (not shown), or can terminate short of the tip so long as it extends along at least about seven-eighths the distance of the length of the reservoir 20 from the contact 30. In another embodiment, the conductive member can actually contact the end of the tip 5, or even extend into a portion of the tip 5. In the depicted embodiment, the tip housing 10 includes a projection 12 that can be used to help align the tip 5 and tip housing 10 when they are seated against the remainder of the cartridge. The projection 12 typically includes at least one aperture (not shown) that permits fluid communication of the electrolyte component between the reservoir and the tip 5.

Figure 2B:
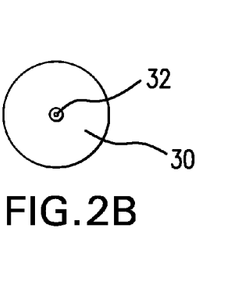
FIG. 2B illustrates an elevation view of an electrical contact according to the invention.

With reference to FIG. 2B, the electrical contact 30 is preferably located outside of the casing 25 but remains in electrical contact with the conductive member 15 or a similar material. The contact 30 depicted in various figures including FIG. 1 is therefore preferably made of the same material as the conductive member 15 as to the portion inside the casing that might contact electrolyte component or off-gases generated therefrom, but preferably a non-conductive material separates the conductive member 15 and the contact 30. Preferably the casing 25 is integrally formed and the conductive member 15 is inserted in an aperture 32 sized only sufficiently to permit the conductive member 15 therethrough so as to minimize loss of electrolyte component. The electrical contact 30 can take any shape so long as it remains electrically conductive, is in contact with the conductive member 15 and fits within the external housing 45 of the test probe. The electrical contact 30 can be made of substantially or entirely the same material as the conductive member 15 or it can be made of the same or similar materials adapted to electrically connect the test probe to the meter, preferably including copper and more preferably nickel-plated copper, such as that commercially available from Braxton Manufacturing Co., Inc. of Watertown, Conn. While such material can be independently selected, in one embodiment it is preferred that the material be the same as the conductive member 15 to minimize corrosion. As further discussed below, the contact 30 must be electrically associated with the top contact 35 (shown in FIGS. 5-6) of the external wire 50 (FIGS. 5-6) so that current can pass between the reservoir 20 and the external wire 50 associated with the meter.

FIG. 3 depicts just the casing 25 that is open at the probe end and in the depicted embodiment is open at the contact/connection end opposite the probe end. The casing 25, along with the tip housing 10 and optionally the contact 30 form the reservoir 20 that contains the electrolyte component. In a non-depicted embodiment, the casing 25 is sealed at the contact 30 end except an aperture 32 for the conductive member 15 of FIGS. 1 and 2A to extend through.

Figure 4:
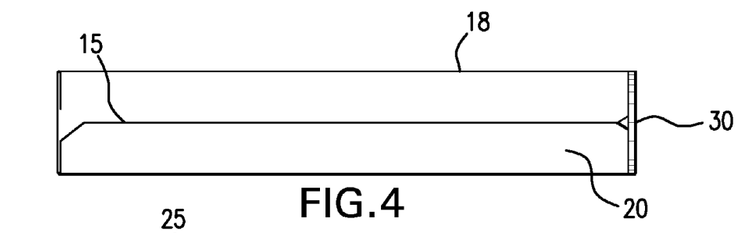
FIG. 4 illustrates a sectional view of a reservoir, a conductive member and electrical contact in a replaceable cartridge according to the invention.

FIG. 4 depicts an embodiment showing the reservoir portion 18 of the cartridge. The reservoir portion 18 includes an electrolyte component 20 and a conductive member 15, which in this embodiment terminates in a less than complete loop at the probe end and forms a circular plane at the opposite end. A casing 25 (shown in FIG. 3) can have the reservoir portion 18 and an aligned, adjacent tip Sand tip housing 10 (shown in FIG. 2A) disposed therein to form a replaceable cartridge.

Figures 5, 6, 7A, 7B:
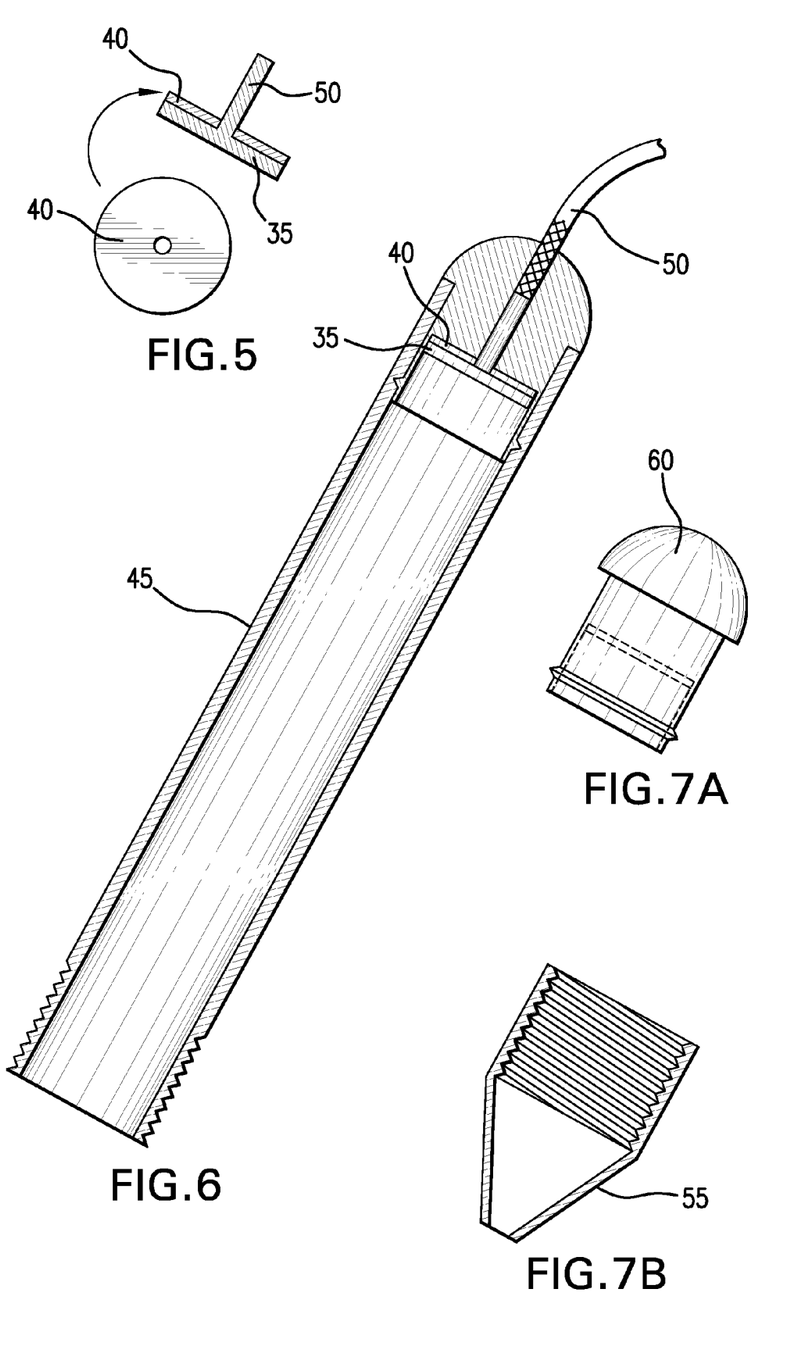
FIG. 5 illustrates a sectional view of an exemplary electrical connection and a seal to be disposed at an end of a cartridge that is opposite a tip according to the invention.
FIG. 6 illustrates a sectional view of a housing that surrounds and can retain a cartridge and a releasable electrical connection according to the invention.
FIG. 7A illustrates a sectional view of the test probe with a portion of the housing that partly forms the closed position, without the releasable electrical connection, according to the invention.
FIG. 7B illustrates a sectional view of the probe end of a test probe with a portion of the housing that partly forms the closed position, without the fibrous tip, according to the invention.

FIG. 5 better illustrates an exemplary electrical connection associated with the contact 30. The electrical connection contains a second electrical contact 35 connected to an external wire 50 that connects to the meter (not shown). Preferably, it also is associated with a gasket 40 that can be formed of a non-conductive component, such as a rubber component, to minimize or avoid loss of current or interference to the current. The second contact 35 can be made of the same or similar materials as the contact 30 or it can be made of the same or similar materials adapted to electrically connect the connection end to the meter, preferably copper and more preferably nickel-plated copper, such as that commercially available from Boker's, Inc. of Minneapolis, Minn. The second contact 35 can have the same or a dissimilar shape as the contact 30 provided that there is sufficient electrical communication therebetween for current flow between the conductive member 15 and the meter. For example, the first and second contacts 30 and 35 can be soldered together, or they can each be planar or substantially planar surfaces that are adjacent to each other preferably with pressure applied by the housing (not shown in FIG. 5) urging the two contacts into closer contact. In a preferred embodiment, a banana connector is used to connect the external wire 50 from the meter to the second contact 35 of the test probe. The electrical connection between the test probe and the meter may be released so as to minimize electrical hazards when changing the replaceable cartridge, or to permit replacement of the entire test probe. Preferably, the external wire 50 is a copper-containing wire although any suitable conventional wire or electrical connector may be used as the external wire 50 to connect the meter with the second contact 35. The connection between the external wire 50 and the second contact 35 is distal (i.e., opposite and away) from the electrolyte and outside of the reservoir 20, so as to minimize or avoid corrosion of the electrical joint between the conductive member, 15 and the external wire 50 and at the contact 30 and second contact 35.

FIGS. 6, 7A and 7B illustrate an embodiment of portions associated with the housing 45 into which the replaceable cartridge 1 and second electrical connection 35 are placed. In a preferred embodiment, the housing 45 includes a top cap 60, a tip cap 55 and a housing body 45. The housing is made of any electrically non-conductive material, such as a plastic component or a glass, or any combination thereof, preferably a plastic polymer such as polyethylene or polypropylene, or a combination thereof. Although not depicted, the housing 45 can be integrally formed with either the top cap 60 or the tip cap 55, since the cartridge 1 can be inserted from either end of the housing body 45. When the top cap 60 is integrally formed, the external wire 50 is releasably connected through a standard plug-in electrical connection once the housing 45 is assembled. As seen in FIG. 6, the second electrical connection 35 associated with the external wire 50 is located inside the housing, adjacent to or even within the zone formed by the top cap 60 of the housing 45. The top cap 60 can be connected to and released from the housing body 45 and optionally and preferably the second electrical contact 35, and this joining and separation to the closed and open positions of the housing 45 can be achieved by any suitable technique available to one of ordinary skill in the art, such as threading, push and turn, spring, or slide mechanism. In addition, or alternatively, the tip cap 55 can be releasably attached to the housing body 45 in any manner that is independently selected from those available, such as described herein for the top cap 60. The tip cap 55 has an aperture for the top of the fiber tip 5 to fit into so that the electrolyte component can be dispensed into the fiber tip 5 that is then placed in contact with the test sample. Indeed, the tip housing 10 can be disposed in the tip cap 55 so as to seat the tip 5 associated with the cartridge 1 into the tip cap 55 so it extends through the aperture and helps align the tip cap 55 as it is moved into a closed position with the remainder of the housing 45. An additional covering can be formed to fit over the exposed portion of the fiber tip 5 so as to avoid drying out of the fiber tip 5, or the tip cap 55 can be sealed at the tip end and used only for sealing the tip where the housing 45 is already formed so as to contain its own tip housing 10. The additional covering can also be releasably attached to the housing through any suitable attachment mechanism as discussed herein.

FIGS. 8A and 8B illustrate an embodiment of the test probe when fully assembled. The housing 45 can take any three-dimensional shape including one that is partially, substantially or entirely cylindrical, spherical, oblong, oval or capsule-shaped. Preferably, the housing 45 is shaped similarly to the component parts that it contains to facilitate the components functioning as described herein. In the depicted embodiment, the housing 45 has a tapered, or recessed, region so as to facilitate a user's grip on the test probe, such that it is partially cylindrical with a recessed portion. As shown in the embodiment depicted in FIG. 8B, the top cap 60 at the connection end is slightly tapered and the portion of the tip cap 55 is tapered inwards towards the probe end. The covering 65 that is operatively associated with the tip cap 55 and/or the housing 45 can be made of any non-conductive material, in one embodiment preferably a plastic and/or rubber material. More preferably, the covering 65 includes a rubber material, such as that commercially available from McMaster-Carr of Chicago, Ill. (e.g., Product No. 4777A14), with a polypropylene encasement that is operatively associated with the tip cap 55 and/or the housing 45.

The housing (including any separate but joinable tip or top cap and covering), the replaceable cartridge and preferably the second electrical connection encompass the test probe. The test probe is portable and able to be carried in a pocket or by hand to the testing sample or adjacent a meter. An integrated file may be attached to the test probe by a clip or some other attaching device, or it may be attached to the adjacent meter body. The integrated file can be used to minimize or remove any coatings or platings that are present on the test sample, such as by scraping or scoring of the coating or plating to increase electrical contact between the tip 5 of the test probe and the precious metal sample to be tested.

The apparatus described herein tests the impurity content of precious metals, and it can advantageously do so across a wide range of impurity contents. The apparatus is adapted to accurately measure purity of, for example without limitation, gold test samples over a range of alloys from 6K to 24K gold, and will accurately and precisely read impurity content even if the sample is gold-plated or washed. These readings will preferably remain accurate and precise until the electrolyte component is depleted, because the apparatus is advantageously designed to minimize or avoid corrosion of its electrical connections.

For example, a replaceable cartridge with a reservoir containing a saturated aqueous solution of ammonium chloride ($NH_4Cl$) in distilled water and a palladium wire, is placed inside the housing and the housing is placed in the closed position by threadedly interconnecting the tip cap and the housing body. The second electrical connection and top cap are connected to the housing body (i.e., the housing) and the replaceable cartridge. After grounding the electrical circuit, preferably by using either a grounding plate on the housing of the meter or a grounding wire, the fiber tip containing a sufficient amount of electrolyte component is placed on or adjacent to the test sample. It should be understood that the test sample must be placed on or in stable contact with the grounding plate, or otherwise grounded using the grounding wire, which can be attached to the sample by any available technique, including without limitation an alligator clip or mini-vise grip, if the sample is too large to fit and remain in contact with a grounding plate associated with the testing apparatus or the associated meter body. When the moistened fiber tip is placed on the test sample, the current generated by the test sample is measured by the meter. For example, when testing a 24 carat (K) gold test sample, this is pure and no impurity content is present. The meter thus measures a low resistance and therefore relatively high current. If the allegedly pure gold test sample contains impurities such as tin, nickel or bronze, or is plated, including a heavy gold wash plating, the meter will detect more resistance and so less current will be registered by the meter. While the meter cannot always clearly indicate the contents of the impurities, the increased resistance from a pure gold standard current clearly indicates that a lower carat test sample is present (i.e. 18K, 14K or 10K gold). When the sample is not pure initially, such as when the sample is 18K or 14K gold, the resistance level of a known 18K or 14K gold sample can be tested or a reference standard checked in a standard table, and then changes in resistance or current flow can show the presence of additional unexpected impurity. Alternatively, the testing apparatus can be used to test the purity of other precious metals, such as platinum or palladium.

Multiple applications and electrical readings can be obtained with a single cartridge or test probe, which can last at least about three months, preferably at least about six months, and in one preferred embodiment at least about one year. Without being bound by theory, it is believed that this can surprisingly be achieved in part because of the corrosion-resistant arrangement of components of the test probe and the arrangement of other aspects of the probe to extend the usable life of the tip. The length of stable readings from a given cartridge or replaceable test probe will depend on various factors including use of a covering to seal the tip, direction of the test probe when stored between uses, length of use for each test, sample tested, temperature, pressure, etc. The apparatus of the invention, however, will last significantly longer than conventional testing devices due to their surprising electrical contact arrangements, their general design including a fibrous tip, and the resultant reduced corrosion achieved by such an arrangement. Thus, by "substantially corrosion resistant" it is meant that the electrical connections will resist corrosion and remain active and precise (without false or significant imprecise readings such as 0.1% errors or greater) over extended periods of time such as at least about 3 months, at least about 6 months, at least about 9 months, and preferably at least about one year, or until such time as the test probe requires replenishment of the electrolyte component.

The above-described apparatus is used to analyze the impurity content of a sample of precious metal or an alloy thereof. The methods used to analyze a precious metal sample are not particularly limited to one technique, manner or skill set. The conductive zone of the testing device, which is preferably portable, is associated or placed into electrical contact with the precious metal-containing sample. The conductive zone, or region where conductivity occurs through electrical contact between the sample and the testing device, preferably is detachable from the rest of the testing device so as to ensure ease of replacement thereof. Once the conductive zone of the portable testing device is attached to the rest of the testing device, is in contact with the sample, and current is able to flow through the conductive zone by use, for example, of a grounding plate or wire as part of the conductive zone, the amount of resistance to that current as emitted by any impurities in the sample can be measured. This can be measured by any suitable meter available to those of ordinary skill in the art, including a meter such as an ohmmeter. Preferably, the measured resistance is displayed to a user through any format including, but not limited to, electronic, print, digital, LCD or analog, or a combination thereof, and can be stored electronically or in print for later review. In one embodiment, a portion of surface contaminants present are removed from the sample, for example by filing, washing or otherwise scratching or scraping the surface of the sample, or a combination thereof, before the sample is contacted by the conductive zone of the testing device. This can advantageously increase the speed, convenience and accuracy of the testing device. In a further embodiment, a file can be integrated into the body of the testing device such as part of the test probe or the meter, so as to eliminate the need to carry multiple items for testing in different locations.

The measured resistance can then be compared to a standard value of electrical measurements to more accurately determine the impurity content of the sample. In one embodiment, the measured resistance can be compared against a pure sample of that type of precious metal, against a known sample having an expected level of impurity of that type of precious metal, against a reference standard for either, or the like. In another embodiment, the type of precious metal or alloy thereof is input into the testing apparatus to provide a more meaningful result in which the measured resistance is more readily compared against a pure sample or another type of reference standard for that inputted type of precious metal or alloy thereof. In this embodiment, the display can therefore indicate the level of impure content or the level of purity of the sample through well-known calculation(s) based on the measured resistance, the inputted type of precious metal or alloy thereof, and based on guidance herein as to the invention. In one embodiment of the invention, the type of precious metal or alloy thereof is input into the testing apparatus to provide a more meaningful result in which the measured resistance is compared against a pure sample or another type of reference standard for that inputted type of precious metal or alloy thereof. In this embodiment, the display can therefore indicate the level of impure content or the level of purity of the sample through well known calculation based on the measured resistance, the inputted type of precious metal or alloy thereof and based on guidance herein as to the invention.

In one embodiment, the precious-metal testing device is able to be readily repaired by an end-user rather than requiring a professional when the test probe is depleted of sufficient electrolyte component, such as through lengthy or heavy use or leaking of the electrolyte component when a user does not use the preferred associated tip covering. Replacement of the cartridge or test probe can also be achieved when a different cartridge containing a different electrolyte component or tip is desired, such as when the tip is smashed, soiled, hardened, or the like, or if certain electrolyte mixtures are determined to work better for certain types of precious metal testing. The method for repairing the precious-metal testing device substantially includes opening the housing of the testing probe or of its component parts to release the relevant component part that retains the electrolyte component, the tip, or the like. In a preferred embodiment, the housing device components are threadedly coupled to one another so as to enable separation of the components upon twisting of the tip cap, top cap, or both, of the housing. As noted elsewhere herein, in a preferred embodiment either the top cap or the tip cap are integrally formed with the housing body, or are separately formed but only one needs to be removed to proceed with the replacement of the electrolyte component. Once a portion of the housing is in the open position, the replaceable cartridge or casing inside the housing can be removed from the test probe and a different replacement cartridge is placed within the housing. The housing is then returned to the closed position, for example without limitation by turning, twisting, pushing or pulling, or a combination thereof depending on the housing design, of its component parts or a mechanism which then holds the component parts together in the closed position. In one embodiment, the mechanism can be any mechanical item which releasably holds the components of the housing together, such as a switch, snap, a locking device or a securing device, or any combination thereof. In a preferred embodiment, the tip cap and top cap of the housing are threaded so as to facilitate re-coupling of the housing portions to each other so as to retain the cartridge or casing therein for use. In a preferred embodiment, a set of instructions to carry out the replacement is associated with the precious-metal testing device. Preferably, the instructions are tailored to the type of interconnections and fastener(s) the components of the housing contain. In another embodiment, instructions can be provided to carry out the method of testing an impurity content in a precious metal-containing sample according to the invention, and are preferably provided with the testing apparatus prepared according to the invention.

The cartridge, housing, or entire test probe can be readily replaced or made replaceable if desired when the tip becomes soiled or smashed, or the electrolyte component depletes so that an insufficient amount is present in the tip. Thus, in one embodiment, the housing body 45 is the casing itself that contains the electrolyte component and a portion of the tip and a portion of the conductive member. Thus, the term "replacement cartridge" can include without limitation any one of the following: (a) the entire test probe up to the external wire; (b) the entire test probe except for the external wire and the second electrical connection; (c) the entire test probe including the housing and all the components contained therein, provided that the housing does not include the external wire, the second electrical connection, and the top cap; or (d) the housing including, or being, the casing, along with the electrolyte component, the conductive member, and the optional but preferably fibrous material included therein, the tip housing and tip, and the electrical contact that is electrically associated with the second electrical contact.

The term "about," as used herein, should generally be understood to refer to both numbers in a range of numerals. For example, "about 1 to 10" should be understood as "about 1 to about 10." Moreover, all numerical ranges herein should be understood to include each whole integer within the range, i.e., 1, 2, 3, 4, 5, 6, 7, 8, 9, and 10.

The term "substantially free," as used herein, generally refers to no more than about 10 weight percent, preferably no more than about 5 weight percent, and more preferably no more than about 2 weight percent of the undesirable component, e.g., epoxy or resin based on the total weight of the tip, or gel based on the total electrolyte component, as appropriate. In one more preferred embodiment, the term means no more than about 1 weight percent, preferably no more than about 0.5 weight percent, and more preferably no more than about 0.1 weight percent, of the undesired component. The term "entirely free" means no more than a trace amount of such undesired material(s) are present, e.g., as an impurity in the test apparatus or a portion thereof.

The foregoing detailed description outlines features of several embodiments so that those of ordinary skill in the art may better understand the various aspects of the present disclosure describing the invention. Those of ordinary skill in the art should appreciate that they may readily use the present disclosure as a basis for designing or modifying other testing apparatus and method details for carrying out the same purposes and/or achieving the same advantages of the embodiments introduced herein. Those of ordinary skill in the art should also realize that such equivalent details do not depart from the spirit and scope of the present disclosure, and that they may make various changes, substitutions and alterations herein without departing from the spirit and scope of the present disclosure. In the drawings, the same or similar elements are denoted by the same or similar reference numerals even though they are depicted in different figures.

What is claimed is:

1. A precious-metal testing apparatus adapted to analyze an impurity content of a precious metal sample, which comprises:
   a test probe having a probe end and a connection end, wherein the test probe comprises a housing and a cartridge comprising a conductive member, a supply of an electrolyte component, and a casing retaining the electrolyte component, a portion of the conductive member, and an end of a fibrous tip at the probe end in fluid communication with the electrolyte component,
   wherein the cartridge is retained by the housing and
   wherein the fibrous tip is electrically conductive when a sufficient amount of the electrolyte component is present therein;
   a meter adapted to measure an electrical resistance of a precious-metal sample through the test probe; and
   an electrical connection that electrically associates the conductive member of the cartridge, which extends through an end thereof opposite the probe end, with an external conductive component that extends to the meter,
   wherein the electrical connection is located outside the casing that contains the electrolyte component.

2. The apparatus of claim 1, wherein a portion of the test probe is replaceable so as to permit replenishment of the supply of the electrolyte component.

3. The apparatus of claim 2, wherein the housing comprises a closed position to retain the cartridge and an open position configured to release the cartridge for replacement thereof.

4. The apparatus of claim 3, wherein the housing comprises a plurality of pieces that can threadedly couple to form the closed position and uncouple to attain the open position.

5. A method for repairing the precious-metal testing device of claim 3 which comprises:
adjusting the housing of the test probe into the open position;
removing the replaceable cartridge from the test probe;
inserting a replacement cartridge within the housing; and
returning the housing to the closed position so as to retain the replacement cartridge.

6. A set of instructions to carry out the method of claim 5 associated with the precious-metal testing device operably associated therewith.

7. The apparatus of claim 1, wherein the conductive member comprises palladium, silver, or a mixture thereof.

8. The apparatus of claim 1, wherein the test probe is releasably connected to the external conductive component.

9. The apparatus of claim 1 where the fibrous tip is at least substantially free of an epoxy.

10. The apparatus of claim 1, wherein the test probe is at least substantially corrosion resistant.

11. The apparatus of claim 1 further comprising an integrated file associated with the test probe for minimizing or removing a contaminant portion from the test sample.

12. A replaceable, precious metal impurity content testing cartridge sized and configured to fit with a test probe housing, which testing cartridge comprises:
a non-conductive casing that comprises:
an electrolyte component present in an amount sufficient to conduct electricity through a portion thereof;
a conductive member electrically associated with the electrolyte component and oriented at least partly along a length of the casing so that a portion of the conductive member extends through the casing so as to minimize loss of the electrolyte component; and
an electrically non-conductive fiber tip disposed at an end of the casing and at least partially contacting the electrolyte component therein via aperture at the end,
wherein the fiber tip is electrically conductive when a sufficient amount of electrolyte component is absorbed therein, and
wherein the portion of the conductive member that extends through the casing is adapted for electrical connection in an environment that is at least substantially free of electrolyte component.

13. The replaceable cartridge of claim 12 further comprising a fibrous material that at least partially surrounds the conductive member in the casing to inhibit the loss of electrolyte component from the casing.

14. The replaceable cartridge of claim 12 wherein the electrically non-conductive fiber tip comprises a plurality of at least substantially parallel elongated fiber portions pressed together.

15. The replaceable cartridge of claim 12 wherein the plurality of fiber strings comprise an acrylic component.

16. The replaceable cartridge of claim 12 wherein the conductive member comprises palladium, platinum, or silver, or a combination thereof.

17. The replaceable cartridge of claim 12 wherein the conductive member comprises a first metal in a core layer and a second, different non-corrosive metal that surrounds the first metal to inhibit or prevent contact between the core layer and the electrolyte component in the casing.

18. The replaceable cartridge of claim 17 further comprising an electrical contact that is disposed at least partly outside the casing and that comprises the same material as the conductive member and is electrically associated therewith.

19. The replaceable cartridge of claim 12 wherein the electrolyte component comprises an aqueous acidic solution.

20. The replaceable cartridge of claim 19 wherein the aqueous acidic solution comprises at least one of ammonium chloride ($NH_4Cl$), hydrochloric acid (HCl), nitric acid ($HNO_3$), or any combination thereof.

* * * * *